(12) United States Patent
Ooyama et al.

(10) Patent No.: US 8,203,705 B2
(45) Date of Patent: Jun. 19, 2012

(54) INSPECTION APPARATUS AND INSPECTION METHOD

(75) Inventors: Masami Ooyama, Hitachi (JP);
Masayuki Hachiya, Tokorozawa (JP);
Rieko Hachiya, legal representative, Tokorozawa (JP); Kimiko Hachiya, legal representative, Tokorozawa (JP);
Kazuhiro Zama, Mito (JP); Keiichi Nagasaki, Hitachinaka (JP)

(73) Assignee: Hitachi-High Technologies Corporation, Tokyo (JP)

( * ) Notice: Subject to any disclaimer, the term of this patent is extended or adjusted under 35 U.S.C. 154(b) by 562 days.

(21) Appl. No.: 12/350,581

(22) Filed: Jan. 8, 2009

(65) Prior Publication Data
US 2009/0187354 A1 Jul. 23, 2009

(30) Foreign Application Priority Data
Jan. 11, 2008 (JP) ................................ 2008-003807

(51) Int. Cl.
*G01N 21/00* (2006.01)
(52) U.S. Cl. .................................. 356/237.1; 356/237.2
(58) Field of Classification Search .... 356/237.1–237.5, 356/614–625
See application file for complete search history.

(56) References Cited

U.S. PATENT DOCUMENTS
| | | | |
|---|---|---|---|
| 6,115,117 A | 9/2000 | Isozaki | |
| 6,201,601 B1 | 3/2001 | Vaez-Iravani et al. | |
| 7,719,671 B2 * | 5/2010 | Yamashita et al. | 356/237.2 |
| 2005/0270522 A1 * | 12/2005 | Miyakawa et al. | 356/237.2 |
| 2007/0182958 A1 | 8/2007 | Manabe et al. | |
| 2007/0201019 A1 * | 8/2007 | Yamashita et al. | 356/237.2 |
| 2007/0211241 A1 | 9/2007 | Aizawa et al. | |

FOREIGN PATENT DOCUMENTS
| | | |
|---|---|---|
| JP | 11-111819 | 4/1999 |
| JP | 11-153549 | 6/1999 |
| JP | 2007-225480 | 9/2007 |
| JP | 2007-240512 | 9/2007 |

OTHER PUBLICATIONS

Japanese Notice of Reasons for Rejection, w/ English translation thereof, issued in Japanese Patent Applcation No. JP 2008-003807 dated Dec. 6, 2011.

* cited by examiner

*Primary Examiner* — Michael P Stafira
(74) *Attorney, Agent, or Firm* — McDermott Will & Emery LLP

(57) ABSTRACT

The invention is directed to detect a warp amount in a real-time manner in a wafer rotating at high speed under inspection. An inspection apparatus includes: a first light irradiating unit for irradiating an object to be inspected with light; a first detector for detecting scattered light from the object to be inspected; a second light irradiating unit for irradiating the object to be inspected with light; a second detector for detecting light reflected from the object to be inspected, of light of the second light irradiating unit; a stage for moving an object to be inspected, which moves the object to be inspected so as to change irradiation positions on the object to be inspected, of the light of the first light irradiating unit and the light of the second light irradiating unit; an inspection coordinate detector for outputting information of coordinates of a position irradiated with light; an elevation control circuit for outputting height information of the object to be inspected on the basis of a detection signal from the second detector; and a data processing unit for calculating a warp amount of the object to be inspected on the basis of the information of the position coordinates from the inspection coordinate detector and the height information from the elevation control circuit.

40 Claims, 10 Drawing Sheets

INSPECTION APPARATUS AND INSPECTION METHOD

BACKGROUND OF THE INVENTION

1. Field of the Invention

The invention relates to a method and apparatus for inspecting an object to be inspected. For example, the invention is suitable for an inspection method and a surface inspection apparatus for detecting a foreign matter, a defect, and the like in an object to be inspected such as a semiconductor wafer, a glass substrate or a ceramic substrate.

2. Description of the Related Art

In the case where a foreign matter or a defect exists in the surface of a semiconductor wafer, it exerts an influence on the yield of a semiconductor device. Consequently, a semiconductor wafer surface inspection has been being performed by a surface inspection apparatus. As conventional techniques for detecting a foreign matter and a defect existing in the surface of a wafer, techniques disclosed in U.S. Pat. No. 6,201,601 and Japanese Patent Application Laid-Open Publication No. 11-153549 (JP-A-11-153549) are known.

U.S. Pat. No. 6,201,601 discloses a surface inspection apparatus for irradiating a wafer with a perpendicular beam and an oblique beam from an illumination optical system using a laser as a light source, collecting scattered light from the wafer by a parabolic mirror, and detecting the collected light by a detector. Scattered light originating from the perpendicular beam and scattered light originating from the oblique beam is split from each other by intentionally introducing an offset between the two radiation beams, using two beams having different wavelengths, or switching the perpendicular radiation beam and the oblique radiation beam on and off alternately. A beam position error caused by a change in sample height is corrected by detecting specular reflection of the oblique radiation beam and changing the radiation direction in accordance with a result of detection of the specular reflection by a mirror.

JP-A-11-153549 discloses a method of inspecting the surface of an object to be measured, by emitting light from a light source via an optical system obliquely to the surface of an object to be measured, receiving scattered light reflected from the surface of the object to be measured, while making the object to be measured and the optical system displaced relative to each other, detecting a foreign matter on the surface of the object to be measured, and recording the coordinate position of the foreign matter. In the method, at the time of detecting a foreign matter on the surface of the object to be measured, height of the object to be measured is measured. By using a height signal of the object to be measured, the coordinate position of the foreign matter is corrected.

A control criterion for a foreign matter and a defect existing in a semiconductor wafer is becoming severer as the size of a semiconductor device is becoming smaller. In recent years, since even a foreign matter adhered to the rear face of a wafer and a rear-face state exert an influence on the yield of a semiconductor device, an inspection for a foreign matter and a defect existing not only in the main face of a wafer but also in the rear face is demanded. In such an inspection, a stage of an edge grip method of handling the main face and rear face of a wafer in a non-contact manner is used. However, since an internal space which makes the main face and rear face in non-contact state is provided and a wafer itself is held by its edges, a large deformation (deflection and warp) occurs in the wafer due to pressure fluctuations in the internal space accompanying self weight and rotation of the wafer. The deformation of the wafer makes both sensitivity of detection of a foreign matter and a defect and the coordinate precision significantly degrade. It is therefore necessary to detect a deformation state under operation and to correct the state in order to maintain the detection sensitivity and coordinate precision.

However, in the conventional techniques, detection of a wafer deformation state while detecting a foreign matter and a defect existing in the wafer is not considered. There is a problem such that it is not possible to determine whether or not the shape of a wafer is in a proper range in order to determine credibility of detection sensitivity and position coordinate precision of a surface inspection apparatus and in order to maintain the performance of detection sensitivity and position coordinate precision. In addition, since correction of the shape of a wafer against the detected deformation state of a wafer is not considered, deformation-following ability of an autofocus mechanism degrades. Due to a focus deviation and an irradiation position deviation of a perpendicular irradiation beam spot and an oblique irradiation beam spot formed on the surface of a wafer, detection sensitivity of a foreign matter and a defect and position coordinate precision degrade. When deformation of a wafer under inspection is conspicuous, a problem occurs such that a small foreign matter and a small defect cannot be detected.

SUMMARY OF THE INVENTION

An object of the invention is to provide an inspection apparatus and method capable of detecting a deformation state of an object to be inspected during an inspection.

Another object of the invention is to provide an inspection apparatus and method for detecting a deformation state of an object to be inspected during an inspection and properly correcting the deformation state of the object to be inspected in accordance with the detected deformation state.

A feature of the invention is detection of a deformation state of an object to be inspected while inspecting the object to be inspected. More concretely, for example, the invention provides an inspection apparatus including: a first light irradiating unit for irradiating an object to be inspected with light; a first detector for detecting scattered light from the object to be inspected; a second light irradiating unit for irradiating the object to be inspected with light; a second detector for detecting light reflected from the object to be inspected, of light of the second light irradiating unit; a stage for moving an object to be inspected, which moves the object to be inspected so as to change irradiation positions on the object to be inspected, of the light of the first light irradiating unit and the light of the second light irradiating unit; an inspection coordinate detector for outputting information of coordinates of a position irradiated with light of the second light irradiating unit; an elevation control circuit for outputting height information of the object to be inspected on the basis of a detection signal from the second detector; and a data processing unit for calculating a deformation state of the object to be inspected on the basis of both the information of the coordinates of a position irradiated with the light of the second light irradiating unit from the inspection coordinate detector and the height information from the elevation control circuit.

Another feature of the invention is to provide a gas port for correcting a shape at the time of detecting the deformation state of the object to be inspected while inspecting the object to be inspected. More concretely, for example, an inspection apparatus includes: a first light irradiating unit for irradiating an object to be inspected with light; a first detector for detecting scattered light from the object to be inspected; a second light irradiating unit for irradiating the object to be inspected with light; a second detector for detecting light reflected from the object to be inspected, of light of the second light irradiating unit; a stage for moving an object to be inspected, which moves the object to be inspected so as to change irradiation positions on the object to be inspected, of the light of the first light irradiating unit and the light of the second light irradiating unit; a gas supplying unit for supplying gas whose flow is controlled to the reverse face of the object to be inspected; an inspection coordinate detector for outputting information of coordinates of a position irradiated with light of the second light irradiating unit; an elevation control circuit for outputting height information of the object to be inspected on the basis of a detection signal from the second detector; and a data processing unit for calculating a deformation state of the object to be inspected on the basis of both the information of the position coordinates from the inspection coordinate detector and the height information from the elevation control circuit.

Another feature of the invention is to detect a deformation state of an object to be inspected while inspecting the object to be inspected, and to control flow of gas for correcting a shape in accordance with a detection result. More concretely, for example, an inspection apparatus includes: a first light irradiating unit for irradiating an object to be inspected with light; a first detector for detecting scattered light from the object to be inspected; a second light irradiating unit for irradiating the object to be inspected with light; a second detector for detecting light reflected from the object to be inspected, of light of the second light irradiating unit; a stage for moving an object to be inspected, which moves the object to be inspected so as to change irradiation positions on the object to be inspected, of the light of the first light irradiating unit and the light of the second light irradiating unit; a gas supplying unit for supplying gas whose flow is controlled to the reverse side of a surface to be inspected of the object to be inspected; an elevation control circuit for outputting height information of the object to be inspected on the basis of a detection signal from the second detector, a data processing unit for calculating a deformation state of the object to be inspected on the basis of both the information of the position coordinates from the inspection coordinate detector and the height information from the elevation control circuit; and a flow controller for controlling flow of gas supplied to the gas supplying unit on the basis of the calculated deformation state.

A further another feature of the invention is an inspection method for irradiating an object to be inspected with a light beam while scanning and for detecting scattered light from the object to be inspected, including: irradiating the object to be inspected with a second-light beam different from the light beam; capturing height information of the object to be inspected by reflection light of the second light beam; controlling height of the object to be inspected to a predetermined position in accordance with the height information; and calculating a deformation state of the object to be inspected on the basis of information of the control to the predetermined position.

A further another feature of the invention is an inspection method for irradiating an object to be inspected with a light beam while scanning and for detecting scattered light from the object to be inspected, including: irradiating the object to be inspected with a second light beam different from the light beam while supplying gas whose flow is controlled to the reverse side of a surface to be inspected of the object to be inspected; capturing height information of the object to be inspected by reflection light of the second light beam; controlling height of the object to be inspected to a predetermined position in accordance with the height information; calculating a deformation state of the object to be inspected on the basis of information of the control to the predetermined position; and controlling flow of gas supplied to the reverse side of the surface to be inspected in accordance with the calculated deformation state.

In one mode of the invention, an inspection apparatus and an inspection method capable of detecting a deformation state of an object to be inspected during an inspection can be provided.

In another mode of the invention, an inspection apparatus and an inspection method capable of detecting a deformation state of an object to be inspected during an inspection and, according to the detected deformation state, correcting properly shape of the object to be inspected can be provided.

DESCRIPTION OF PREFERRED EMBODIMENT

An inspection method and inspection apparatus of the invention can be applied to, for example, a flat plate-shaped object to be inspected such as a semiconductor wafer, a glass substrate for a liquid crystal panel or a TFT module, and a sapphire substrate or ceramic substrate for use in a sensor, an LED, or the like. In the following embodiments, a surface inspection apparatus and a surface inspection method using a semiconductor wafer as an object to be inspected will be described as an example.

First Embodiment

Figure 1:
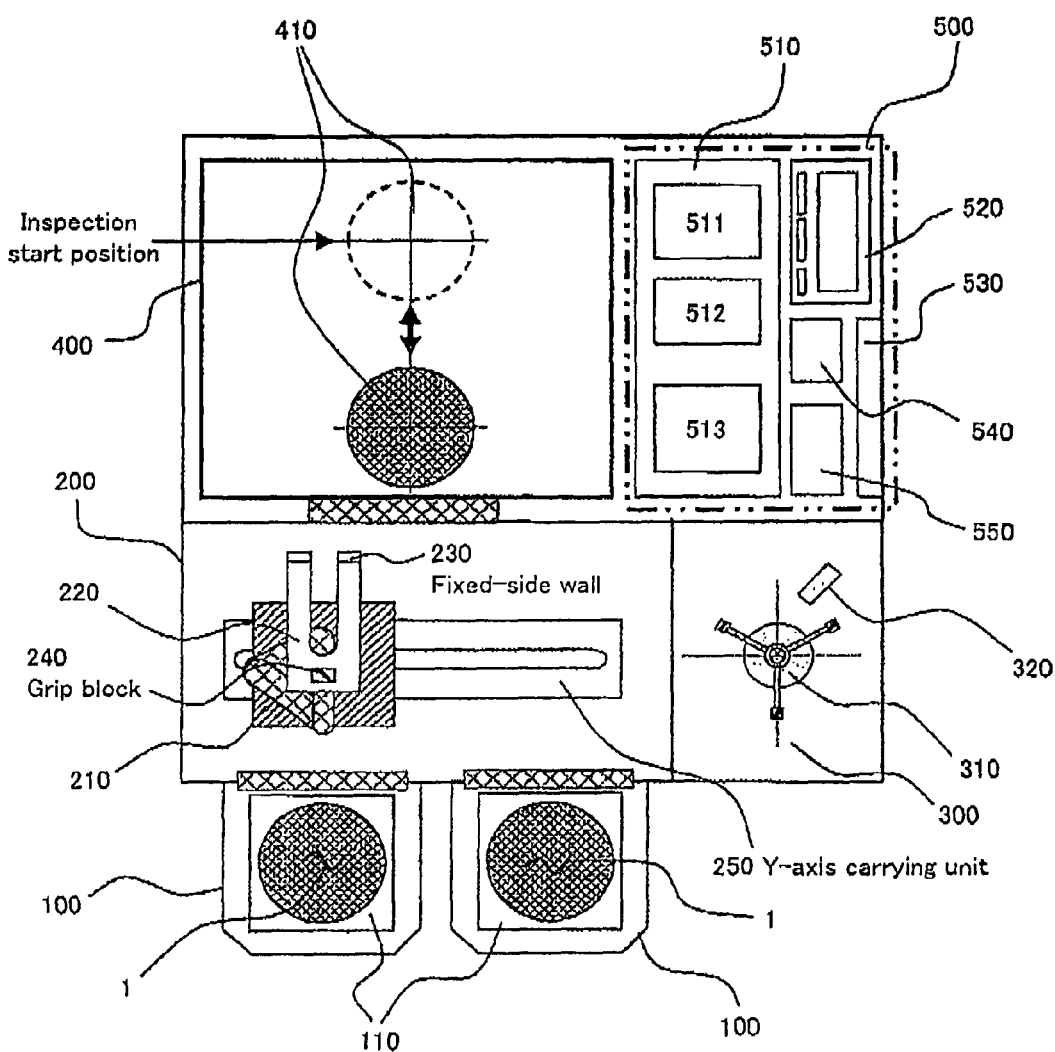
FIG. 1 is a plan view showing a schematic configuration of a surface inspection apparatus as an embodiment of the invention.

FIG. 1 is a plan view showing a schematic configuration of a surface inspection apparatus as an embodiment of the invention. The surface inspection apparatus includes a plurality of load ports 100 having the function of mounting a wafer (object to be inspected) 1, a carrying unit 200, a pre-alignment unit 300, an inspection unit 400, and a data processing unit 500. On the load port 100, a wafer pod 110 for housing the wafer 1 is mounted. On all of the plurality of load ports 100, wafer pods 110 for inspecting process can be mounted. A part of the plurality of load ports 100 can be used for separating and collecting a wafer 1 determined as defective.

The carrying unit 200 includes a carrying apparatus 210 for carrying the wafer 1, and a Y-axis carrying unit 250. The carrying apparatus 210 has a handling arm 220 of an edge grip type being driven on the basis of an instruction signal from the data processing unit 500 and handling the face and the rear face of the wafer 1 in a non-contact manner. The handling arm 220 includes, in an almost U-shaped fork, a fixed-side wall 230 and a grip block 240 disposed so as to face the fixed-side wall 230. By pressing the end portion (edge) of the wafer 1 with the fixed-side wall 230 and the grip block 240, the wafer 1 itself is gripped by the edge and carried among load ports 100a and 100b, the pre-alignment unit 300, and the inspection unit 400.

The pre-alignment unit 300 includes a mounting stand 310 for supporting the end portion of the wafer 1 in three or four points and a sensor 320 for detecting the outer periphery of the wafer 1. The mounting stand 310 on which the wafer 1 is mounted detects the outer periphery by the sensor 320 while rotating the wafer 1 and pre-aligns the position (almost the center position) of the wafer 1 and the notch position. By supporting the wafer 1 by the surrounding end portion, the surface reverse to the surface to be inspected of the wafer 1 can be pre-aligned in a non-contact manner.

Above the pre-alignment unit 300, a receiving stand of a not-shown inverting unit is disposed. At the time of inspecting the rear face of the wafer 1 as a surface to be inspected, the wafer 1 is reversed by the unit. By the inverting unit, substrate carriage with the face or the rear face of the wafer 1 being set as a surface to be inspected can be performed.

The data processing unit 500 includes a controller 510, an input device 520 such as a keyboard, a touch panel, or a mouse, a display device 530 such as a CRT or a flat panel display, an output device 540 such as a printer, and an external storage 550 for controlling an external medium. The controller 510 includes an arithmetic processing unit 511, a storage 512 such as an HDD, and a control device 513, and controls the entire surface inspection apparatus on the basis of an instruction from the input device 520. Setting conditions, an inspection result, and the operation state of the inspection apparatus are displayed by the display device 530. Their respective informations are outputted via the output device 540.

Figure 2:
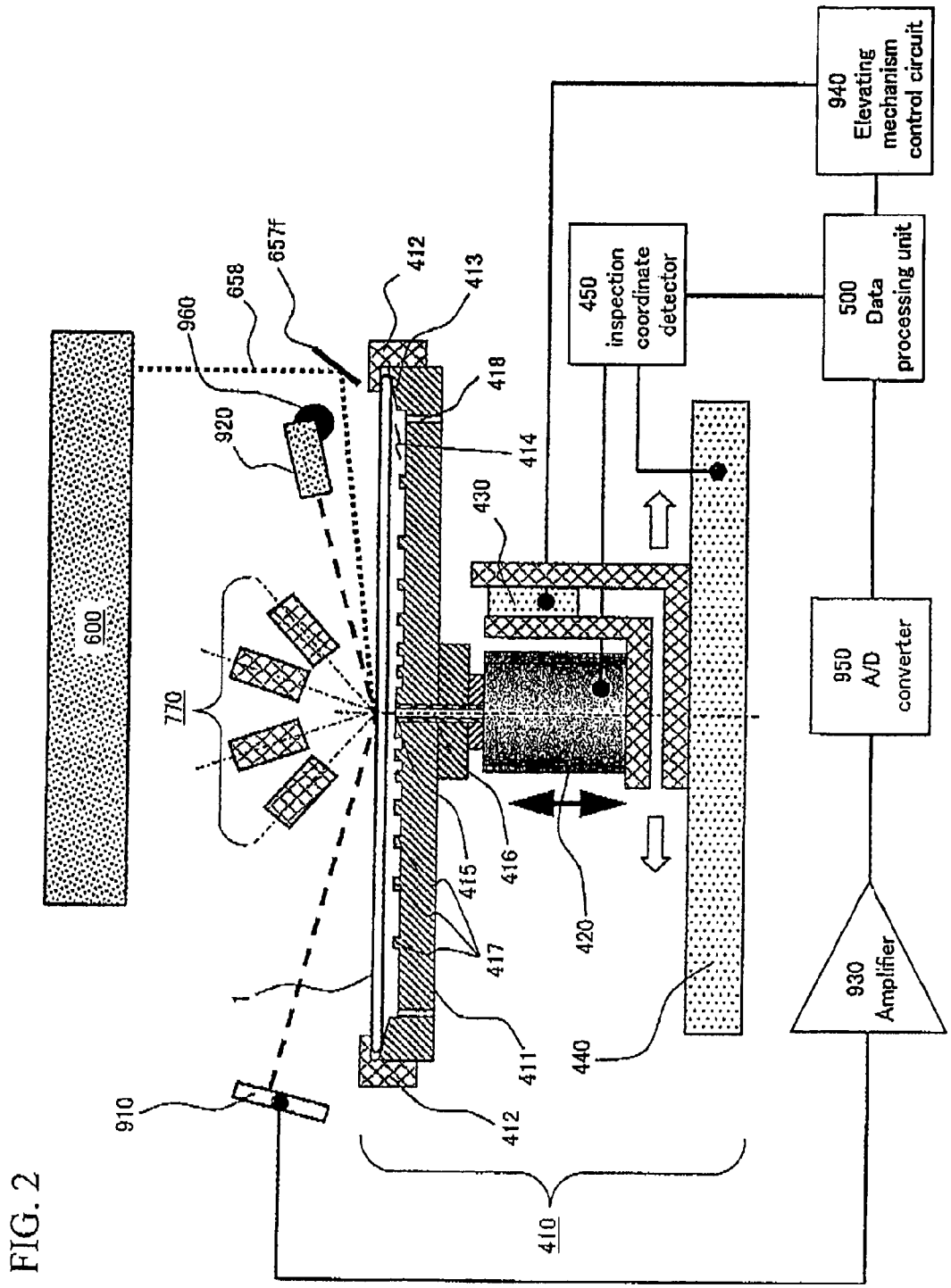
FIG. 2 is a front view showing an internal configuration of an inspection unit in the surface inspection apparatus.

FIG. 2 is a vertical cross-sectional view showing the internal configuration of the inspection unit 400 illustrated in FIG. 1. The inspection unit 400 includes a stage 410 for moving an object to be inspected, for scanning the wafer 1, a first light emitting unit 600 for emitting a light beam (illumination beam) 658 such as a visible laser beam or an ultraviolet laser beam, a first detector 770 for detecting scattered light from the surface to be inspected of the wafer 1, and a height position controller 900 (which will be described later) for controlling the surface to be inspected to a focus position.

Figure 6:
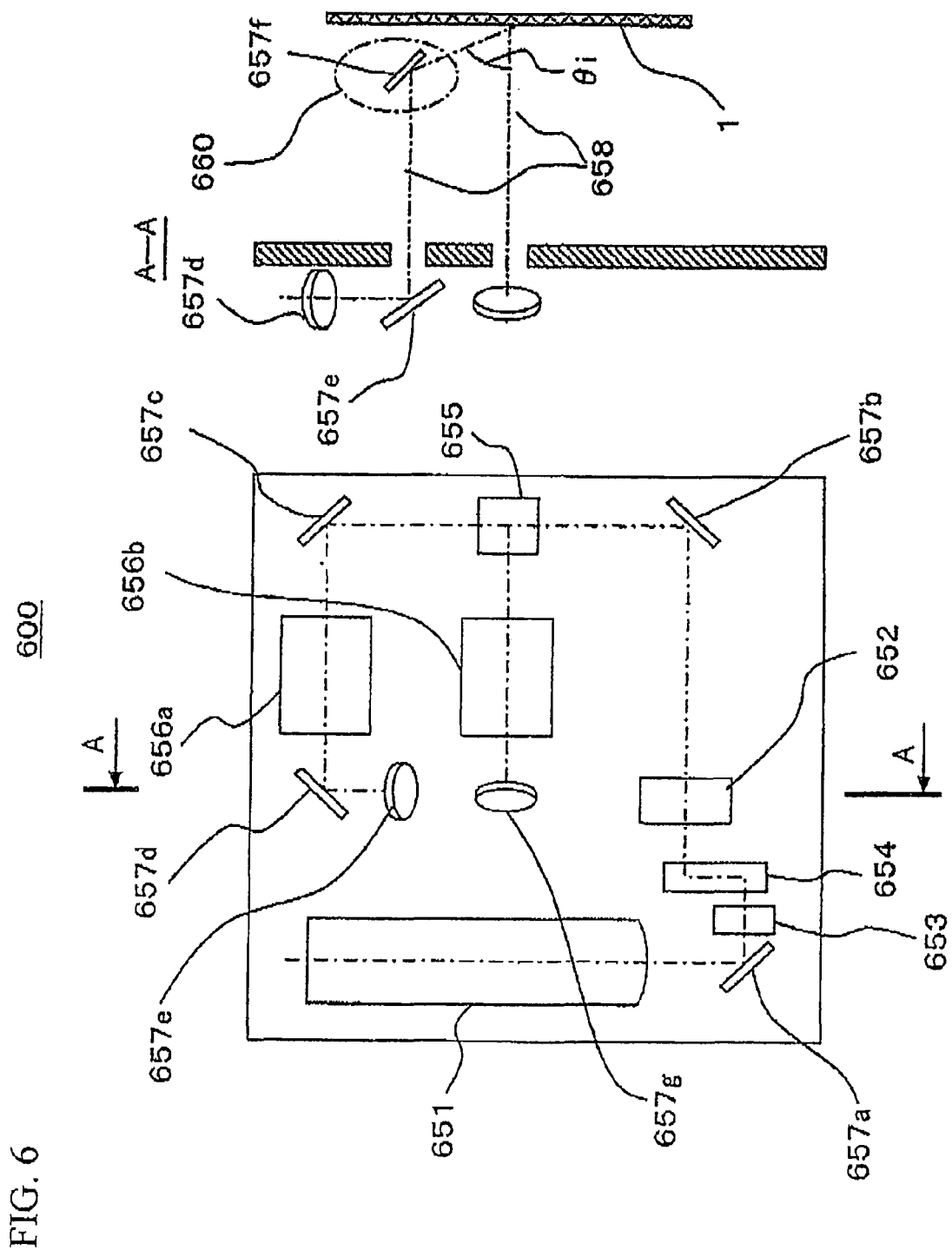
FIG. 6 is a plan view showing a light irradiating unit related to the invention.

FIG. 6 is a diagram showing a schematic configuration of the first light emitting unit 600. The first light emitting unit 600 (irradiating mechanism) has a laser light source 651 for generating the light beam 658, a shutter 652 for blocking the laser beam, an attenuator 653 for adjusting intensity of the light beam 658, an optical axis correcting mechanism 654 for correcting an optical axis shift of the light beam 658, an irradiation direction switching mechanism 655 for switching the irradiation direction of the light beam 658 to an oblique direction or a perpendicular direction, beam shaping mechanism 656a and 656b for shaping the cross-sectional shape of the light beam 658 to a predetermined shape, and mirrors 657a to 657g for changing the course of the light beam 658.

The light beam 658 emitted from the laser light source 651 passes through the mirror 657a and is adjusted to energy density adapted for an inspection by the attenuator 653. The light beam 658 passes through the optical axis correcting mechanism 654 for correcting an optical axis shift, and through the mirror 657b, and is transmitted to the irradiation direction switching mechanism 655. The irradiation direction switching mechanism 655 includes optical elements such as a mirror, a parallel plate glass, and a half mirror. By selecting any of the optical elements, the optical path of the light beam 658 can be changed. The optical path of the light beam 658 is changed to a first projection light optical system effecting perpendicular illumination when the mirror is selected, to a second projection light optical system effecting oblique illumination when the parallel plate glass is selected, and an optical path branched to the first and second projection light optical systems effecting composite irradiation of the perpendicular illumination and the oblique illumination when the half mirror is selected.

In the first projection light optical system effecting perpendicular illumination, by the irradiation direction switching mechanism 655, the course is switched toward the beam shaping mechanism 656b. The light beam 658 is shaped to a sectional shape adapted for the purpose of the inspection and, after that, emitted to the wafer 1 via the mirror 657g at a high elevation angle (using the wafer surface as a reference).

In the second projection light optical system effecting oblique illumination, after passing through the irradiation direction switching mechanism 655, the course is switched by the mirror 657c toward the beam shaping mechanism 656a. The light beam 658 is shaped to a sectional shape adapted for the purpose of the inspection and, after that, emitted to the wafer 1 via the mirrors 657d, 657e, and 657f at a low elevation angle. The illumination angle (elevation angle) is controlled to a predetermined elevation illumination angle $\theta i$ by an output unit 660 made of both the mirror 657f and an irradiation angle control mechanism (not shown).

In the composite irradiation of the perpendicular illumination and the oblique illumination, the branched optical beams 658 are applied to almost the same position in the wafer 1 via the two projection light optical systems. By different elevation illuminations from different elevation angles or composite illumination from a plurality of elevation angles, a characteristic amount (directivity) of a scattered light distribution with respect to the kind of a foreign matter and the kind of a defect is emphasized, and the performance of discriminating the kind of a foreign matter and the kind of a defect can be improved.

Figure 7:
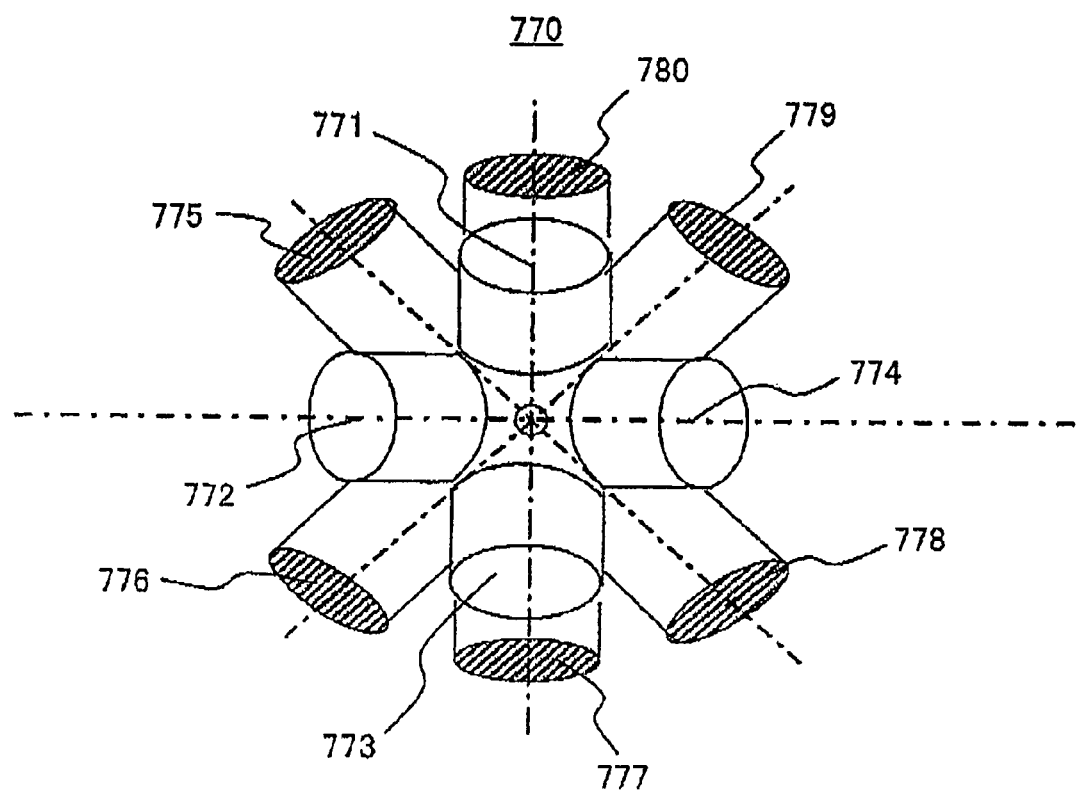
FIG. 7 is a top view showing a schematic configuration of a first detector related to the invention.

FIG. 7 shows an example of layout, seen from above, of a first detector 770 illustrated in FIG. 2. The first detector 770 is made of a group of PMTs (photomultipliers) 771 to 780 disposed at a plurality of elevation angles and azimuths, which are roughly divided in two groups in terms of elevation angle.

The PMTs 771 to 774 as a group of high-elevation detectors are disposed in positions of elevation angles larger (higher) than those of the PMTs 775 to 780 as a group of low-elevation detectors (using the wafer surface as a reference). The PMTs 771 to 774 in the group of the high-elevation detectors are disposed at elevation angles of about 30 degrees or larger (using the wafer surface as a reference), preferably, in the range of 35 degrees to 65 degrees in order to capture light scattered from crystal defects including a COP (Crystal Originated Particle) and OSF (Oxidation induced Stacking Fault) and from structural defects such as a scratch and a crack.

The four PMTs 771 to 774 in the group of the high-elevation detectors are disposed in a plurality of azimuths in angles of about 90 degrees in the circumferential direction so as to be able to efficiently capture scattered light in three modes of forward scattering, side scattering, and back scattering from a foreign matter kind or a defect kind. The number of azimuths is not limited to four. According to kinds of foreign matters and kinds of defects to be discriminated, the PMTs can be disposed in such azimuths that the characteristic amount (directivity) of each of scattered light distributions can be easily captured.

The elevation angles of the PMTs 775 to 780 as a group of low-elevation detectors are set to almost 30 degrees or less (using the wafer surface as a reference), preferably, in the range of 5 degrees to 20 degrees in order to receive mainly scattered light from foreign matters. The six PMTs 775 to 780 in the group of the low-elevation detectors are disposed in a plurality of azimuths at angle intervals of about 60 degrees in the circumferential direction so as to be able to efficiently capture both scattered light in three modes of forward scattering, side scattering, and back scattering from a foreign matter kind or a defect kind, and scattered light emitted in intermediate azimuths. The number of azimuths is not limited to six. According to kinds of foreign matters and kinds of defects to be discriminated, the PMTs may be disposed in azimuths at which the characteristic amount (directivity) of each of scattered light distributions can be easily captured.

The first detector 770 can detect total eight azimuths of the PMTs 775 to 780 in the low-elevation detector group and the PMTs 771 to 774 in the high-elevation detector group, and can efficiently detect the characteristic amount (directivity) of the scattered light distribution with respect to the azimuth. The PMTs 773 and 777 and the PMTs 771 and 780 are disposed at different elevation angles in almost the same azimuth so that the characteristic amount of the scattered light distribution with respect to the elevation angle can be detected. The characteristic amounts of distributions of scattered light from a foreign matter kind or a defect kind are captured by the PMTs disposed in the eight azimuths, and detection signals from the PMTs are computed, thereby enabling discrimination between a foreign matter and a defect and further the kind of the foreign matter or the defect to be performed.

Precision and processing speed of the discrimination between a foreign matter and a defect can be improved by the combination of the projection light optical system and the first detector 770. For example, to detect a foreign matter, the combination of oblique illumination by the second projection light optical system and the PMTs 775 to 780 in the low-elevation detector group is preferable. On the other hand, to detect a defect, it is preferable to select perpendicular illumination of the first projection light optical system or oblique illumination of the second projection light optical system in accordance with the kind of the defect to be discriminated, and to combine the selected illumination with the PMTs 771 to 774 in the high-elevation detector group.

Further, to discriminate between a foreign matter kind and a defect kind at high speed, it is preferable to combine the composite irradiation of the first and second projection light optical systems and the composite detection of different elevation angles of the PMTs 771 to 774 in the high-elevation detector group and the PMTs 775 to 780 in the low-elevation detector group and to obtain the characteristic amount (directivity) of scattered light by arithmetic processing.

Referring again to FIG. 2, the stage 410 for moving an object to be inspected includes a chuck 411 on which the wafer 1 is mounted, retaining nails 412 for locking the wafer 1 by its end portion, a rotating mechanism 420 for rotating the chuck 411, an elevating mechanism 430 for controlling the height of the wafer 1, and a back-and-forth driving mechanism (linear driving mechanism) 440 for moving the wafer almost in parallel along with the chuck 411, the rotating mechanism 420, and the elevating mechanism 430.

The rotating mechanism 420 comprises a rotating device (not shown) such as a spindle motor, and can detect an angle coordinate ($\theta$ coordinate) in the circumferential direction of the wafer 1 by a $\theta$ position detecting device (not shown) such as an internally-provided optical-reading-type rotary encoder. The back-and-forth driving mechanism 440 has therein a linear encoder of the optical-reading-type and can detect the position coordinate (r coordinate) in the radial direction of the wafer 1.

By the rotating mechanism 420 and the back-and-forth driving mechanism 440, the surface to be inspected of the wafer 1 is spirally or circularly scanned with the light beam 658 emitted from the first light emitting unit 600. When a foreign matter or a defect exists in the scan path of the light beam 658, scattered light according to the foreign matter or defect is emitted. By detecting the scattered light by the first detector 770, the existence of the foreign matter or defect is detected. A signal of the scattered light detected by the first detector 770 is stored in the storage 512 in the data processing unit 500 so as to be associated with signals of the angle coordinate and the position coordinate from the rotary encoder and the linear encoder, which signals are outputted from an inspection coordinate detector 450, and is subjected to arithmetic processing. On the basis of the intensity of the detected scattered light, the size of the foreign matter or defect is identified. On the basis of the coordinate signals from the inspection coordinate detector 450, the coordinates of the foreign matter or defect in the wafer 1 are identified.

The chuck 411 has a recessed shape having a ring-shaped rim 413 along the shape of the wafer 1. In the rim 413 disposed at the outer periphery, an inclined plane which is inclined downward to the inside of the chuck 411 is formed. The end portion (edge) of the wafer 1 itself is supported by the inclined plane of the rim 413. By pressing the end portion on the side of the surface to be inspected of the wafer 1 by the retaining nail 412, the wafer 1 is locked to the chuck 411. Between the surface of the chuck 411 and the reverse face of the surface to be inspected of the wafer 1, an internal space 414 via the rim 413 is formed. By the internal space 414, the non-contact state between the reverse face of the surface to be inspected and the chuck 411 is maintained. By the edge grip mechanism, occurrence of adhesion of a foreign matter and a defect in the reverse face of the surface to be inspected is prevented, so that the surface inspection on the face and the rear face of the wafer 1 can be conducted.

In an almost center of the chuck 411, a gas supply part 415 is disposed. The gas supply part 415 supplies gas such as $N_2$, Ar, He, or air via a gas supply path 416 internally provided in both the chuck 411 and the rotating mechanism 420. In the surface of the chuck 411, ring-shaped air gap forming parts 417 each having a flat part in its top face are disposed in a position lower than the rim 413. The plurality of air gap forming parts 417 are formed sparsely in the area of the surrounding part of the chuck 411 and densely toward the area of the center part. The disposition of the air gap forming parts 417 is adjusted so that the pressure distribution in the internal space 414 has a high pressure in the area of the center part of the wafer 1 and a low pressure in the surrounding area. A deflection or warp caused by the self weight of the wafer 1 can be corrected with a small gas flow.

A plurality of exhaust ports 418 for exhausting the gas in the internal space 414 to the rear surface side of the chuck 411 are provided near the rim 413 of the chuck 411.

The gas supplied from the gas supply part 415 transmits pressure to the reverse face of the wafer 1 in accordance with the pressure distribution in the internal space 414 adjusted by the air gap forming parts 417 and is exhausted to the outside of the chuck 411 via the exhaust ports 418.

Consequently, the inside in the internal space 414 surrounded by the wafer 1, the chuck 411 body, and the rim 413 is maintained in a predetermined pressure distribution, an air gap of a predetermined amount is always formed between the air gap forming parts 417 and the wafer 1, and a deflection and warp of the wafer 1 can be corrected.

Figure 3A:
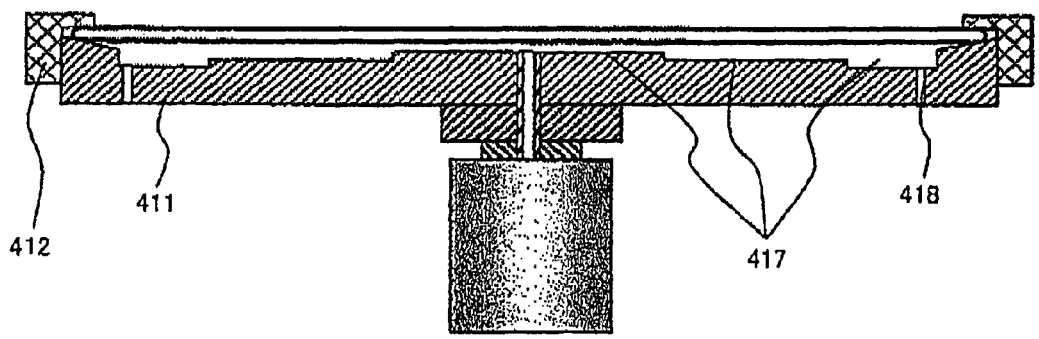
FIG. 3A shows a chuck having an air gap forming part made by a plurality of steps.
Figure 3B:
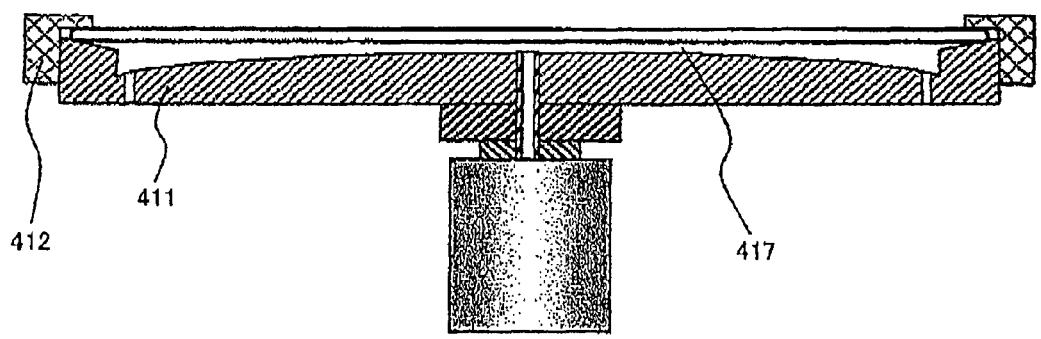
FIG. 3B shows a chuck having an air gap forming part having a projected curve.

In the chuck 411 of the embodiment, the pressure distribution is adjusted by the plurality of air gap forming parts 417. A similar effect can be obtained by an air gap forming part 417 formed by a plurality of steps disposed so that the internal space 414 is widened toward the outside as shown in FIG. 3A, or an air gap forming part 417 having a projected curved surface having a predetermined curvature as shown in FIG. 3B. The shape of the air gap forming part 417 may be obtained by processing the chuck 411 body or generated by combining processed other elements.

Figure 4:
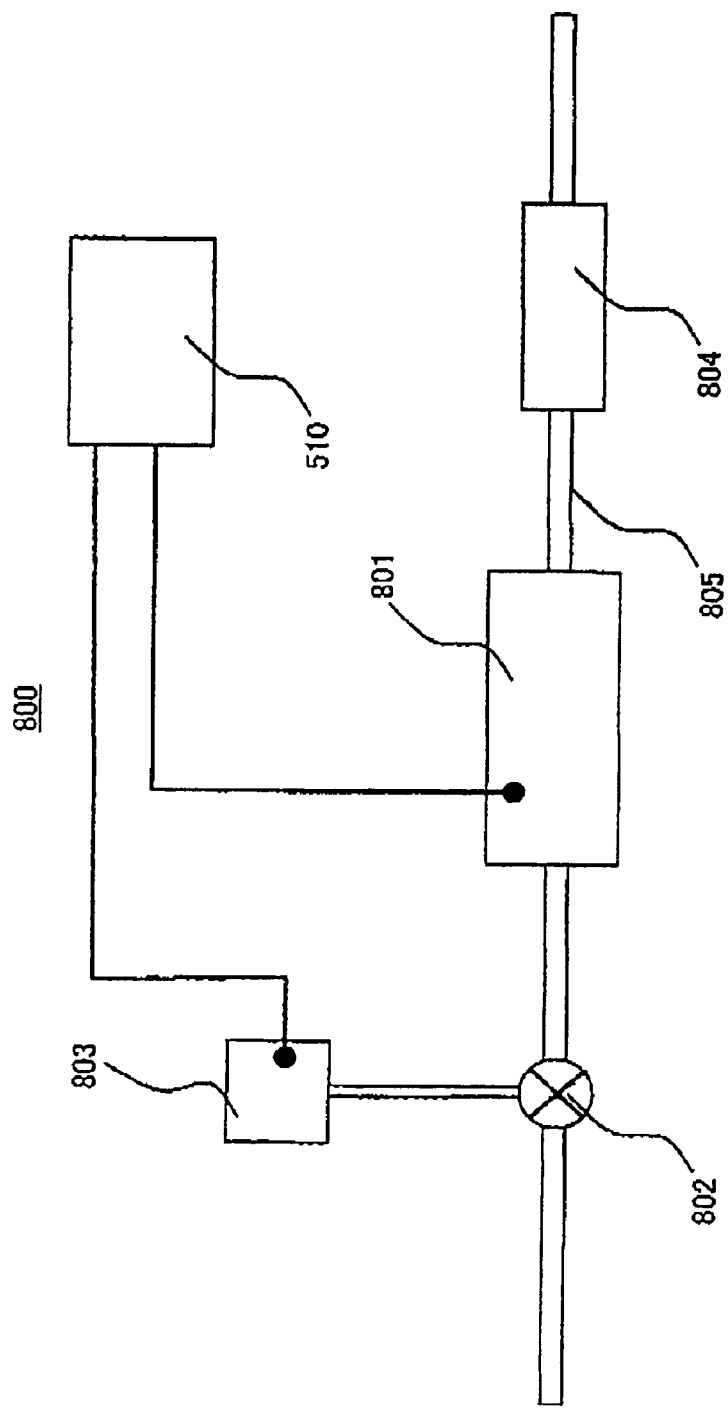
FIG. 4 is a diagram showing a schematic configuration of a gas supply system related to the invention.

FIG. 4 shows a schematic configuration of a gas control system 800 for supplying gas to the reverse face of the wafer 1. The gas control system 800 supplies gas to the internal space 414 of the side grip mechanism to correct a deflection or warp of the wafer 1. The gas control system 800 has a flow controller 801 such as an MFC (Mass Flow Controller) for controlling gas flow, a shutoff valve 802 such as an air valve for opening/closing a gas supply path, an electromagnetic valve 803 for controlling supply of compressed air for opening/closing the shutoff valve 802, a filter 804 for removing dusts in the supply gas, and a pipe 805 for connecting the pipe elements. The pipe 805 is preferably subjected to internal polishing in order to suppress adhesion of a foreign matter to the reverse face of the inspection surface.

The gas control system 800 controls a gas supply timing and supply flow on the basis of an instruction from the controller 510.

At the time of inspecting the wafer 1, the carried wafer 1 is locked by the retaining nail 412 to the chuck 411. After that, a whole close signal is transmitted from the controller 510 to the flow controller 801, and a flow control valve (not shown) in the flow controller 801 is closed.

Subsequently, an open signal to the electromagnetic valve 803 is transmitted. The valve is opened to send the compressed air to the shutoff valve 802, and the gas supply path is opened. After that, a flow setting signal is transmitted to the flow controller 801, slow-up is performed while gradually increasing the opening of the flow control valve, and the flow is controlled to a predetermined flow.

When the inspection is finished, a close signal is transmitted to the electromagnetic valve 803 to close the electromagnetic valve 803 and exhaust the compressed air in the inside, and the shutoff valve 802 is closed. By closing the gas supply path, supply of gas is stopped. After that, locking of the retaining nail 412 is released, and the wafer 1 is carried out to the load port 100 by the carrying unit 200.

It is desirable to use compressed air as the gas supplied to the internal space 414 from the view point of suppressing running cost. However, a gas whose purity and dew point are controlled, for example, $N_2$ or the like is desirable from the viewpoint of suppressing contamination on the reverse face of the inspection surface.

Figure 5:
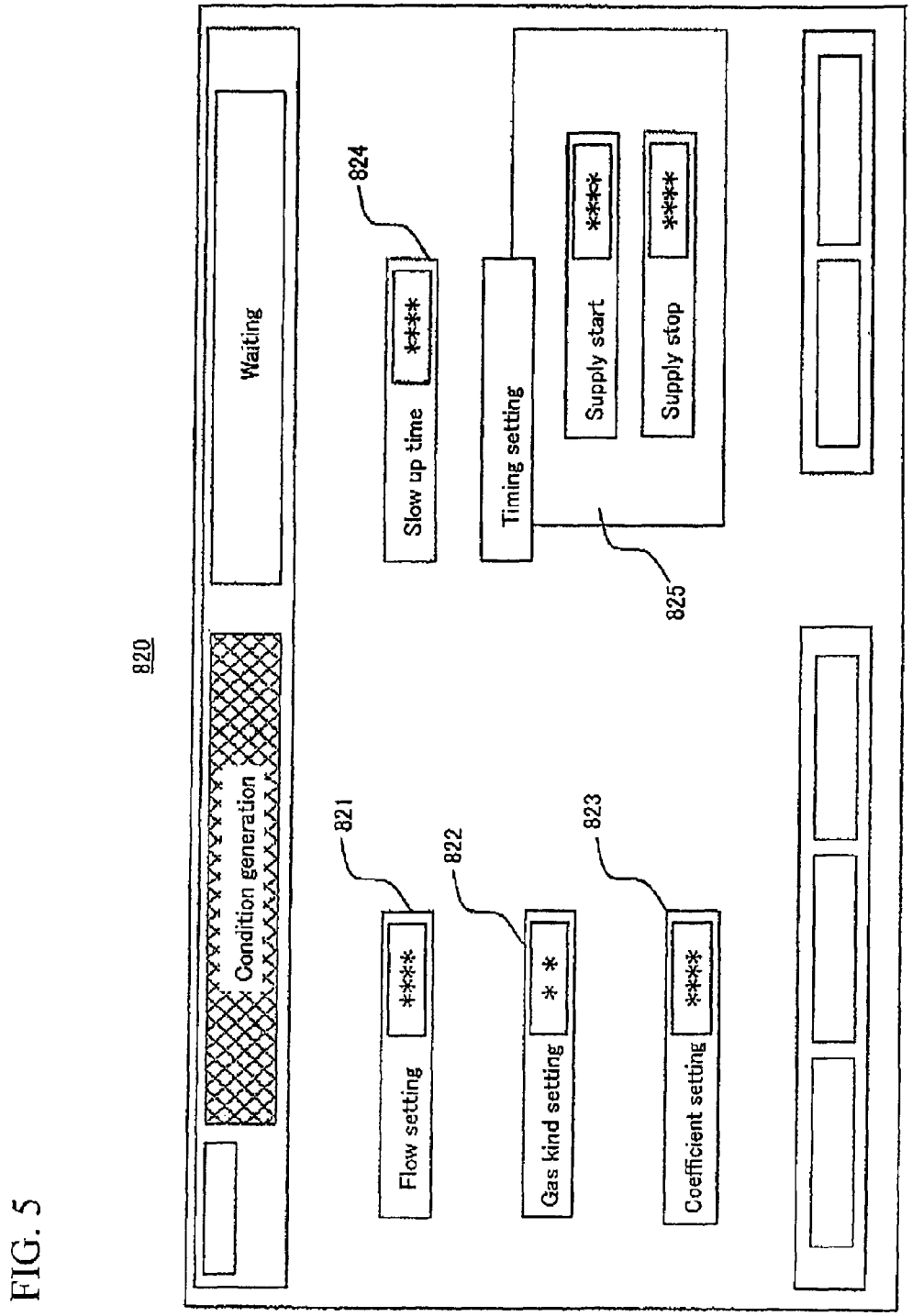
FIG. 5 is a diagram showing a setting screen for controlling the gas supply system related to the invention.

FIG. 5 shows a setting screen 820 for controlling the gas control system 800. The setting screen 820 is displayed on the display device 530 of the data processing unit 500, and the information of the setting screen 820 is registered on the storage 512.

The setting screen 820 comprises a flow setting and displaying part 821 for setting and displaying flow of gas supplied, a kind selecting and displaying part 822 for selecting and displaying the kind of gas, a flow correcting and displaying part 823 for correcting and displaying the flow which changes according to the kind of gas, a slow-up setting and displaying part 824 for setting and displaying slow-up time until the flow reaches a predetermined flow, and a timing setting and displaying part 825 for setting and displaying timings of supplying and stopping the gas.

The flow correcting and displaying part 823 multiplies a set value of the flow setting and displaying part 821 by a coefficient determined according to the kind of gas, and outputs the resultant signal. For example, the MFC is corrected with $N_2$ gas and, generally, makes the flow controller 801 output a flow setting signal multiplied by a heat loss coefficient called a conversion factor.

The timing setting and displaying part 825 controls gas supply start with delay time of 0.5 to 5 seconds using the time point when the wafer 1 is locked to the chuck 411 as a base point. Using the time point when the surface inspection on the wafer 1 is finished and the rotational speed of the rotating mechanism 420 becomes a predetermined rotational speed or less as a base point, gas supply stop is controlled after delay time of 0.5 to 5 seconds. As long as the delay time for stabilizing the operation can be set, the base points of supply and stop of gas are not limited to the above. Any base points may be employed as long as the timings of supply and stop can be controlled.

Although the setting is made on the flow correcting and displaying part 823 via the input device 520 in the embodiment, the coefficient may be automatically changed when the gas kind is selected in the kind selecting and displaying part 822. The setting display or selection display may be performed via the input device 520, or it is also possible to use pressure-sensitive means or the like as the input means on the setting screen 820 and to enter the setting on the screen.

Figure 8:
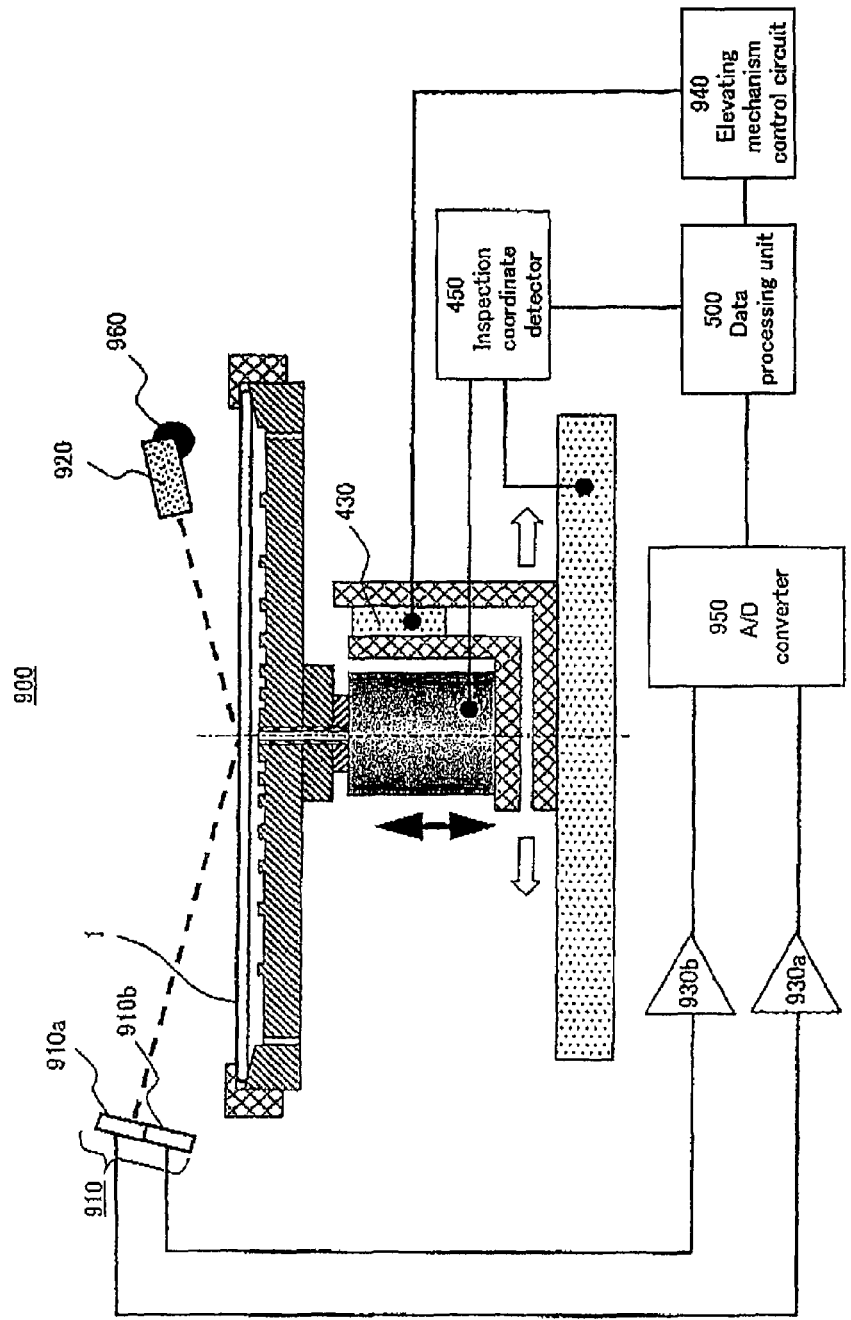
FIG. 8 is a front view showing a schematic configuration of a height position controller in the case of using a two-segmented sensor.

FIG. 8 is a schematic configuration diagram of the elements related to the height position controller 900, extracted from the vertical cross section of the inspection unit 400 shown in FIG. 2. The height position controller 900 detects height information of the neighborhood of the inspection location in the wafer 1 corrected by the gas control system 800 and determines whether the correction is proper or not. Subsequently, the height position controller 900 controls vertical movement position of the inspection location which has been able to be corrected by the gas control system 800 to a predetermined height position. Further, the height position controller 900 calculates a warp state of the wafer 1 under the surface inspection and can check whether the correcting condition of the gas control system 800 is proper or not.

The height position controller 900 includes a second light emitting unit 920 for irradiating the inspection surface of the wafer 1 with light used for detecting a vertical movement position, a second detector 910 for detecting reflection light (specular reflection) of the second light emitting unit 920 and for outputting inspection surface height information (electric signal) of the wafer 1, amplifiers 930a and 930b for amplifying the electric signal from the second detector 910, an A/D converter 950 for converting analog signals from the amplifiers 930a and 930b to digital signals, the data processing unit 500 for processing the digital signals and for outputting an electric signal (control signal) which controls the inspection surface height, and an elevating mechanism control circuit 940 for driving the elevating mechanism 430 on the basis of the control signal from the data processing unit 500.

The second detector 910 is constructed by a photoelectric conversion element. In the embodiment, a two-segmented sensor is used as the second detector 910. It is sufficient for the second detector 910 to detect the position of reception of reflection light from the second light emitting unit 920. A CCD or the like also can be used.

As the light source of the second light emitting unit 920, a light source for emitting light of a wide band or white light is used. In some cases, a laser light source of a single wavelength or the like can hardly obtain reflection light due to the thickness of a film formed on the inspection surface of the wafer 1. Due to the film thickness interference, reception of specular reflection of the second detector 910 is hindered, and an inconvenience occurs such that the vertical movement position of the inspection surface of the wafer 1 cannot be detected. Since the wavelength dependency of reflectance variously varies according to the film thickness and its substance, the light source of the second light emitting unit 920 of the present embodiment is a light source of a wide band (350 to 700 nm) for emitting light from UV light to a visible light range, or a light source for emitting light including wavelengths of a wide range such as white light. With the light source, even if specular reflection cannot be obtained at a specific wavelength, reflection light can be received from another wavelength, and the vertical movement position can be detected stably. As the white light source, for example, a white laser, a white light emitting diode, a xenon lamp, a mercury lamp, a metal halide lamp, a halogen lamp, or the like can be used.

Light emitted from the second light emitting unit 920 is applied near the light beam 658 of the first light emitting unit 600 and is applied ahead on the scan path in which the light bean 658 travels. It is preferable to determine the interval between the light and the light beam 658 in accordance with response speed of the elevating mechanism from the viewpoint of improving precision of height control. The interval can be controlled by an irradiation position control mechanism 960 provided for the second light emitting unit 920. A deviation of the coordinates from the light beam 658 is computed by the data processing unit 500 and corrected to the irradiation coordinates of the second light emitting unit 920.

Light emitted from the light source passes through the second light emitting unit 920 and is applied to the inspection surface of the wafer 1 corrected by the gas control system 800. Therefore, the inspection surface of the wafer 1 is spirally or circularly scanned with the illumination light of the second light emitting unit 920 like the light beam 658. While changing the coordinates in the wafer 1, reflection light from the inspection surface accompanying irradiation of the illumination light is received by the second detector 910, and height position information of the inspection surface at the coordinates is outputted as an electric signal.

Figure 9:
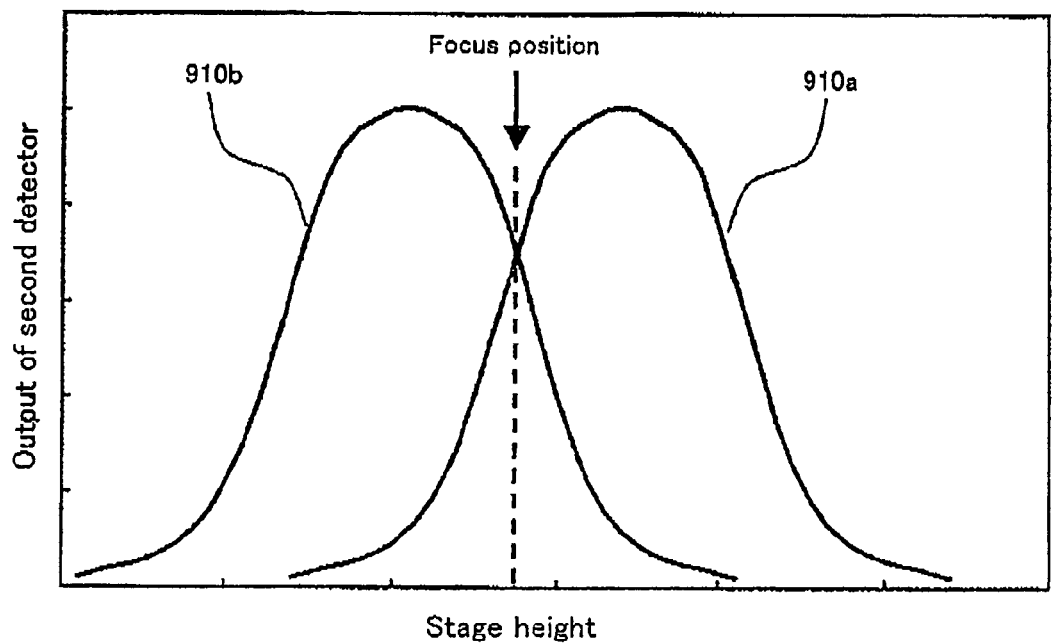
FIG. 9 is a diagram showing the relation between inspection plane height and sensor output in the ease of using a two-segmented sensor.

FIG. 9 shows the relation between height of the inspection surface of the wafer 1 and output from the second detector 910. As described above, it shows an example in which a two-segmented sensor is used as the second detector 910.

The two-segmented sensor comprises an upper sensor 910*a* and a lower sensor 910*b*. The two-segmented sensor changes a detection signal to be outputted, in accordance with the focus position of reflection light, which position varies according to the vertical movement position of the inspection surface of the wafer 1.

Both of the sensors have an upwardly projected output curve with respect to the height of the inspection surface. An electric signal outputted from the upper sensor 910*a* becomes the maximum value on the high position side of the inspection surface of the wafer 1, and that from the lower sensor 910*b* becomes the maximum value on the low position side. Therefore, the cross point between signals outputted from the upper sensor 910*a* and the lower sensor 910*b*, that is, the position in which the output signals becomes the same is detected as the height of the inspection surface of the wafer 1 to be controlled. In the embodiment, predetermined height of the inspection surface to be controlled is set to the focus position. The light beam 658 of each of the first and second projection light optical systems is adjusted to form a predetermined beam spot at the predetermined height, and the second detector 910 is disposed so as to detect the predetermined height.

Electric signals of height position information outputted from the upper sensor 910*a* and the lower sensor 910*b* are amplified by the amplifiers 930*a* and 930*b*, respectively, and transmitted to the A/D converter 950. The analog electric signal of the analog height position information is converted by the A/D converter 950 to a digital electric signal. The electric signals are outputted to the data processing unit 500. The data processing unit 500 performs arithmetic processing on the basis of the electric signals and detects a positional deviation (differential signal) from the predetermined height of the inspection surface.

Subsequently, the data processing unit 500 outputs a control signal for correcting the positional deviation to the elevating mechanism control circuit 940. The elevating mechanism control circuit 940 drives the elevating mechanism 430 on the basis of the control signal to control the inspection surface to the predetermined height of the inspection surface. The elevating mechanism 430 has therein a driving device such as a pulse motor. The elevating mechanism control circuit 940 outputs a drive signal (pulse) to the elevating mechanism 430 until the detected positional deviation decreases to a predetermined value, to control the inspection surface to the predetermined height.

The drive signal outputted from the elevating mechanism control circuit 940 to the driving device is stored in the storage 512 of the data processing unit 500 so as to be associated with signals of the angle coordinate and the position coordinate of the inspection location in the wafer 1, which are outputted via the inspection coordinate detector 450. By arithmetic processing, a warp state of the wafer 1 is calculated.

For example, the travel distance of the vertical movement for one pulse of the drive signal can be obtained from specifications of mechanical elements related to the pulse motor and its driving. Therefore, by sequentially tracing the movement from the start point of the coordinates to the end point on the basis of the coordinates scanned by irradiation light of the second light emitting unit 920 and the output history of the corresponding drive signal, the distance (deviation amount) between the predetermined inspection surface height and an actual inspection location with respect to the coordinates is obtained. That is, the warp state of the wafer 1 can be obtained.

It is also possible to use an output from the A/D converter 950 as it is before being shifted to the correction of the predetermined height of the inspection surface, use a signal from the A/D converter 950 based on the upper sensor 910*a* as A, use a signal from the A/D converter 950 based on the lower sensor 910*b* as B, and obtain the distance by the following equation 1.

$$H = \alpha(A-B)/(A+B)$$   Equation 1

(A+B) expresses the sum of reflection light received by the second detector 910. By dividing (A−B) as the differential signal between the upper sensor 910a and the lower sensor 910b by (A+B), the influence due to a change in the light reception amount is reduced. α denotes a correction factor of the vertical movement amount. It is sufficient to preliminarily obtain a change amount with respect to the drive signal or the travel distance in accordance with the kind of the film and the film thickness. H denotes distance to the predetermined height of the inspection surface. The sign of H shows the positional relation of highness or lowness to the predetermined height.

The value of H computed by the data processing unit 500 is stored in the storage 512 of the data processing unit 500 so as to be associated with signals of the angle coordinate and the position coordinate of the inspection location in the wafer 1 outputted via the inspection coordinate detector 450 by a method similar to the above. By the processing of computing the H value corresponding to the coordinates, the warp state of the wafer 1 is calculated. In the case where a translucent film is formed on the inspection surface of the wafer 1, there is a case that the interface under the film, that is, the Si surface is regarded as an inspection surface. In such a case, it is preferable to provide an offset value and perform a control with a signal to which the offset value signal is added (height detection correcting means). For example, in the calculating method, it is sufficient to add an output signal corresponding to the offset value to the positional deviation (difference signal). It is sufficient for calculating means to be described later to set the offset value in the term of the difference signal by setting α(A−B)/(A+B) in Equation 1 to α(A−B+C)/(A+B).

Figure 10:
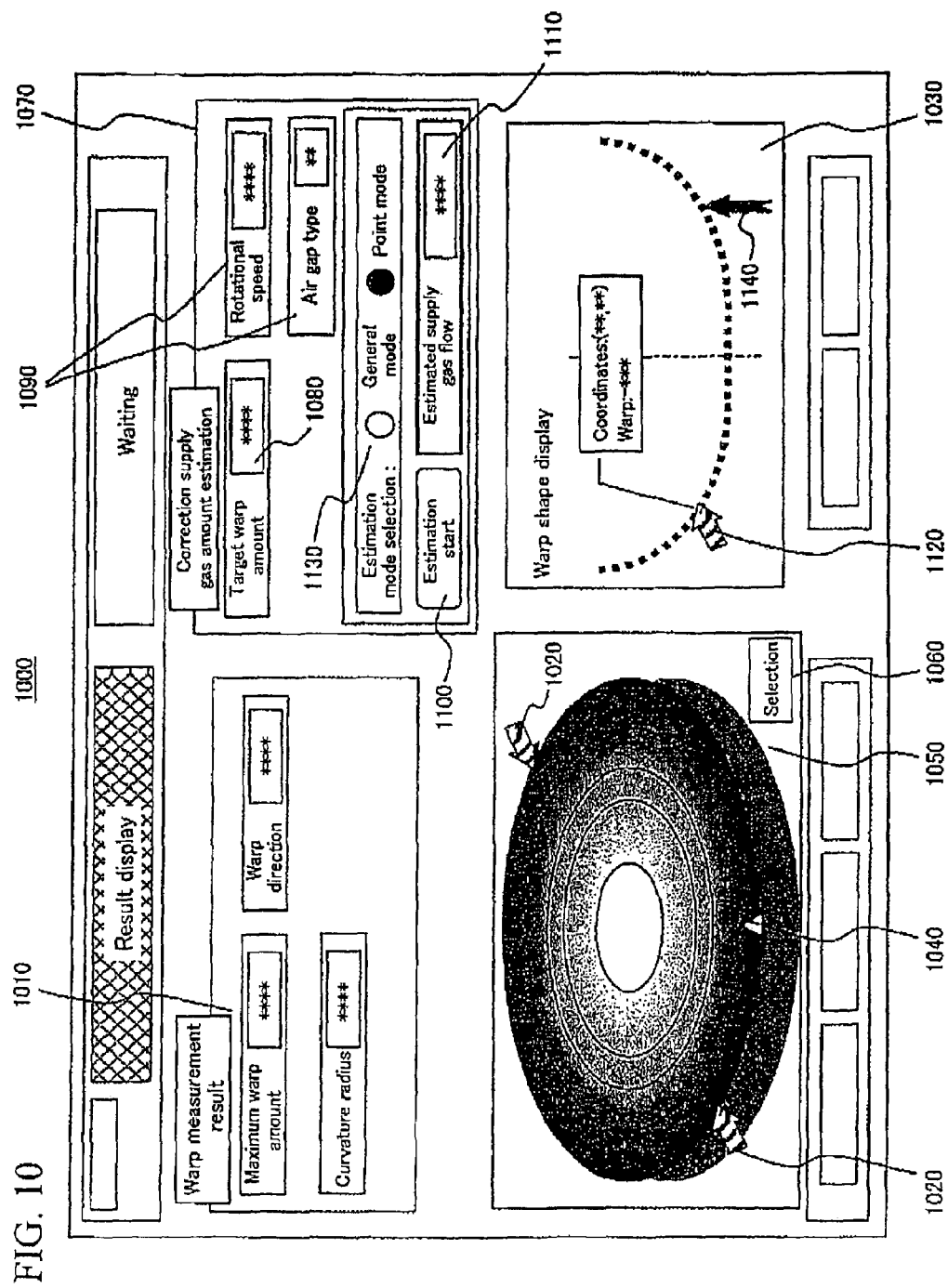
FIG. 10 is a diagram showing a schematic configuration of a display screen for estimating a warp measurement result and a gas supply amount in the invention.

FIG. 10 shows outline of a display setting screen 1000 for displaying a warp state of the entire inspection surface of the wafer 1 detected by the height position controller 900, analyzing the warp state, and simulating a correction supply gas amount. The display setting screen 1000 is displayed on the display device 530 of the data processing unit 500 and can be operated via the input device 520.

In a left upper part of the screen, a result display function 1010 for indicating a numerical value of a warp obtained from measurement is disposed and, for example, the maximum warp amount, curvature radius, the direction of the warp, and the like are displayed. As the curvature radius, curvature radius in a designated direction sandwiched by two pointers 1020 is calculated and displayed. The profile of the warp amount in this direction is displayed by a shape display function 1030.

By selecting an arbitrary position in the profile with a pointer 1120, the coordinates of that point and its numerical value of the warp are displayed (point display function).

The direction of the warp indicates whether the shape of the warp is upwardly projected or downwardly projected. For example, upward projection is displayed as −, and downward projection is displayed as +.

In a left lower part, a warp state display function 1050 is disposed. To unify the positional relation of the wafer 1, a base point 1040 such as a notch or orientation flat is disposed and displayed at a predetermined screen position. The image of the warp state is displayed so that the warp state of the plane of the wafer 1 can be recognized at a glance by 3D display, contour display, shade image display, color display, or the like. The display mode is not limited and can be selected by a display selection function 1060 including a display method other than the above-described display methods.

In a right upper part, a supply gas amount estimation function 1070 for examining setting conditions of the correction supply gas amount is disposed with respect to the measurement result of the warp state. The supply gas amount estimation function 1070 comprises a target setting function 1080 for setting a target value of a warp amount, and some condition setting functions 1090 for setting conditions such as rotational speed of the rotating mechanism 420 and shape of the air gap forming parts 417. By entering an arbitrary numerical value via the input device 520 and clicking a processing instruction function 1100, a correction supply gas amount for converging the warp amount to the target one is calculated. The estimated correction supply gas amount is displayed via a result display function 1110.

The supply gas amount estimation function 1070 has two estimation modes. In one of the modes, for the whole wafer 1, the warp amount is converged to a target value. In the other mode, the warp amount of an arbitrary designated place in the profile is converged to the target value. The estimation mode can be selected by an estimation node selection function 1130. The designated place in the profile can be instructed by a pointer 1140.

The details of the process flow of the surface inspection apparatus in the embodiment will now be described.

The surface inspection on the inspection surface of the wafer 1 starts in response to an execution instruction to an inspection program on the display device 530. The wafer 1 in the wafer pod 110 is handled by the carrying apparatus 210 in the carrying unit 200 and carried to the pre-alignment unit 300.

In the case where the rear face of the wafer 1 is an inspection surface, the wafer 1 is mounted once on the inverting unit and turned upside down. The wafer 1 is mounted on the mounting stand 310 of the pre-alignment unit 300. In the case where the face is the inspection surface, the wafer 1 is mounted as it is onto the mounting stand 310 of the pre-alignment unit 300.

The wafer 1 mounted on the mounting stand 310 is subjected to coarse position correction (pre-alignment) in respect to both an almost center position in the wafer 1 and the position of the notch. Subsequently, the wafer 1 is handled again to the inspection unit 400 by the carrying apparatus 210. The wafer 1 handled to the inspection unit 400 is mounted on the chuck 411 and locked to the chuck 411 by the retaining nail 412.

Subsequently, under the setting conditions of the gas supply setting screen 820, the controller 510 outputs an instruction signal to the gas control system 800 and supplies warp correction gas to the reverse face of the inspection surface of the wafer 1 via the gas supply path 416 and the gas supply part 415. A warp or swell in the wafer 1 due to self weight is corrected by the warp correction gas. The stage 410 for moving an object to be inspected moves to an inspection start position while maintaining the state.

In response to an inspection start instruction from the controller 510, the back-and-forth driving mechanism 440 for emitting the light beam 658 to an almost center of the wafer 1 preliminarily calculated and the elevating mechanism 430 via the height position controller 900 are controlled to perform a start point position correction in the surface inspection.

In parallel with the start point position correcting operation, the rotating mechanism 420 starts rotating the chuck 411 and accelerates increase in the rotational speed. By parallel process of the start point position correcting operation and the rotational speed accelerating operation, required time for the surface inspection is shortened, and the throughput is improved.

The controller 510 controls the rotating mechanism 420 so that the rotational speed reaches predetermined rotational speed in consideration of the timing of completion of the position correcting operation so that the two operations are completed almost synchronously. After the rotational speed reaches the predetermined rotational speed, the rotational speed is held almost constant.

By almost linearly moving the back-and-forth driving mechanism 440 in one-axis direction while irradiating the inspection surface of the wafer 1 rotated at high speed with the light beam 658, the light beam 658 relatively moves spirally, swirly, or circularly to scan the inspection surface at high speed (scanning mechanism). On the other hand, the height position controller 900 emits illumination light of a second irradiation unit 720 ahead on the scan path in which the light beam 658 travels, captures height information of the inspection location in the wafer 1, and controls the inspection location irradiated with the light beam 658 to the height of the focus position.

Scattered light generated from a foreign matter or a defect by the irradiation of the light beam 658 is received by the first detector 700 and analyzed together with the relative travel position information (r coordinate and θ coordinate) of the back-and-forth driving mechanism 440 and the rotating mechanism 420 outputted via the inspection coordinate detector 450 by the data processing unit 500, and the size of the foreign matter or defect and the position coordinates in the wafer 1 are obtained. Similarly, the height information of the inspection location captured by the height position controller 900 is analyzed together with the relative travel position information (r coordinate and θ coordinate) of the back-and-forth driving mechanism 440 and the rotating mechanism 420 outputted via the inspection coordinate detector 450 by the data processing unit 500, and the size of the warp or swell and the warp state in the wafer 1 are obtained. The information of the foreign matter, defect, and warp is stored in the storage 512 with the ID unique to the wafer 1.

By the height position control to the focus position, in the perpendicular irradiation of the first projection light optical system, the beam spot diameter of the light beam 658 is maintained properly, and detection sensitivity is improved. In the oblique irradiation of the second projection light optical system, not only the detection sensitivity but also precision of the coordinates of the foreign matter or defect are improved. Further, in the projection light optical system using both the first and second projection light optical systems, the detection sensitivity is improved and, in addition, false information can be reduced.

The wafer 1 inspected is handled again by the carrying apparatus 210 and housed into the wafer pod 110 of the load port 100.

Although a PMT (photomultiplier) is used for the first detector 700 in the embodiment, the invention is not limited to the PMT. Any photoelectric converting element for converting detected light to an electric signal, such as APD (Avalanche Photodiode), a CCD (Charge Coupled Device), an EM-CCD (Electron Multiplier CCD), a CMOS, or an APS (CMOS Active Pixel Sensor) can be used.

Description has been given using the surface inspection apparatus related to manufacture of a semiconductor device as an example and the semiconductor substrate (wafer) as an object to be inspected. However, the technique of the invention is not limited to a semiconductor substrate but can be used in the field in which a warp amount of a wafer rotating at high speed under inspection has to be detected in a real time manner. Irrespective of the material of the substrate, any plate-shaped substrate such as a glass substrate for use in a liquid crystal panel or a TFT module, or a sapphire substrate for use in a sensor or an LED can be used. The invention is not limited to the manufacturing process of a semiconductor device but can be widely applied to surface inspection apparatuses in various manufacturing processes of various sensors, hard disks, liquid crystal panel display devices, and the like.

DESCRIPTION OF REFERENCE NUMERALS

1 wafer (object to be inspected)
100 load port
110 wafer pod
200 carrying unit
210 carrying apparatus
220 handling arm
230 fixed-side wall
240 grip block
250 Y-axis carrying unit
300 pre-alignment unit
310 mounting stand
320 sensor
400 inspection unit
410 stage for moving object to be inspected
411 chuck
412 retaining nail
413 rim
414 internal space
415 gas supply part
416 gas supply path
417 air gap forming part
418 exhaust port
420 rotating mechanism
430 elevating mechanism
440 back-and-forth driving mechanism
450 inspection coordinate detector
500 data processing unit
510 controller
511 arithmetic processing unit
512 storage
513 control device
520 input device
530 display device
540 output device
550 external storage
600 first light emitting unit
651 laser light source
652 shutter
653 attenuator
654 optical axis correcting mechanism
655 irradiation direction switching mechanism
656*a*, 656*b* beam shaping mechanisms
657*a* to 657*g* mirrors
658 light beam
660 output unit
710, 910 second detectors
720, 920 second light irradiation units
770 first detector
771 to 780 PMTs
800 gas control system
801 flow controller
802 shutoff valve
803 electromagnetic valve
804 filter
805 pipe
820 setting screen
821 flow setting and displaying part
822 kind selecting and displaying part
823 flow correcting and displaying part
824 slow-up setting and displaying part 825 timing setting and displaying part
900 height position controller
930a, 930b amplifiers
940 elevating mechanism control circuit
950 A/D converter
960 irradiation position control mechanism
1000 display setting screen
1010 result display function
1020, 1120, 1140 pointers
1030 shape display function
1040 base point
1050 warp state display function
1060 display selection function
1070 supply gas amount estimation function
1080 target setting function
1090 condition setting function
1100 process instruction function
1110 result display function
1130 estimation mode selection function

The invention claimed is:

1. An inspection apparatus comprising:
a first light irradiating unit for irradiating an object to be inspected with a first irradiating light;
a first detector for detecting a first scattered light from the object;
a second light irradiating unit for irradiating the object with a second irradiating light;
a second detector for detecting a second scattered light from the object;
a stage for moving the object to first and second irradiation positions to receive the first and second irradiating lights, respectively;
an inspection coordinate detector for detecting information of coordinates of a position on the object irradiated with the second irradiating light;
an elevation control circuit for outputting height information of the object based upon a detection signal from the second detector; and
a data processing unit for acquiring a deformation state of the object based upon the outputted height and coordinate information.

2. The inspection apparatus according to claim 1, wherein the data processing unit uses an offset value corresponding to a translucent layer provided on the object to acquire the deformation state.

3. The inspection apparatus according to claim 1, wherein the data processing unit acquires at least one of: a warpage amount of the object, a curvature of the warpage, and a direction of the warpage.

4. The inspection apparatus according to claim 1, wherein the data processing unit includes memory for storing information about an anomaly of the object and information about the deformation state.

5. The inspection apparatus according to claim 1, further comprising:
a gas supplying unit which supplies the object with gas from a backside of the object.

6. The inspection apparatus according to claim 5, wherein the data processing unit executes a simulation for supplying the gas.

7. The inspection apparatus according to claim 5, further comprising:
an edge-grip-system which mounts the object, wherein:
an edge-grip-system comprises a plurality of bumps arranged on a plane facing the backside of the object, and
the plurality of bumps are more tightly-packed towards a center of the object.

8. The inspection apparatus according to claim 7, wherein:
the edge-grip-system further comprises a rim for mounting a edge portion of the object, and
the bumps are arranged at a position lower than a position of the rim.

9. The inspection apparatus according to claim 8, further comprising:
an exhausting aperture for exhausting the gas,
wherein the exhausting aperture is arranged between the rim and the bumps.

10. The inspection apparatus according to claim 5, wherein the gas supplying unit supplies the gas to change a warpage of the object to a target warpage.

11. The inspection apparatus according to claim 5, further comprising:
a flow control unit which changes flow of the gas.

12. The inspection apparatus according to claim 11, further comprising:
a pipe for supplying the gas;
a first valve which gates a path of the pipe; and
a second valve which controls the first valve.

13. The inspection apparatus according to claim 12, wherein the first valve is operated by compressed air and the second valve is an electromagnetic valve which controls supply of the compressed air.

14. The inspection apparatus according to claim 12, wherein the pipe is polished.

15. The inspection apparatus according to claim 11, wherein the flow control unit further comprises a filter arranged at a flow path of the gas.

16. The inspection apparatus according to claim 11, wherein the flow control unit changes the flow of the gas according to a type of the gas.

17. The inspection apparatus according to claim 16, wherein the flow control unit changes the flow by using a conversion-factor as a function of the type of the gas.

18. The inspection apparatus according to claim 11, further comprising:
a chuck which mounts the object,
wherein the flow control unit supplies the gas by providing a delay time until the chuck mounts the object.

19. The inspection apparatus according to claim 11, further comprising:
a rotating unit which rotates the object,
wherein the flow control unit stops supplying the gas providing a delay time until a number of rotations of the rotating unit decreases below a predetermined number of rotations.

20. The inspection apparatus according to claim 1, wherein the second light irradiating unit includes a broadband-light-source which outputs from visible-light to UV-light, or a white light source.

21. A method of inspecting an object, the method comprising steps of:
irradiating an object with a first irradiating light from a first light irradiating unit;
detecting a first scattered light from the object by a first detector;
irradiating the object with a second irradiating light from a second light irradiating unit;
detecting a second scattered light from the object by a second detector;
moving a stage on which the object is mounted to first and second irradiation positions to receive the first and second irradiating lights, respectively;

detecting information of coordinates of a position on the object irradiated with the second irradiating light;

outputting height information of the object based upon a detection signal from the second detector; and acquiring a deformation state of the object by a data processing unit based upon the outputted height and coordinate information.

22. The method according to claim 21, further comprising the step of:

using an offset value corresponding to a translucent layer provided on the object to acquire the deformation state.

23. The method according to claim 21, further comprising the step of:

acquiring at least one of: a warpage amount of the object, a curvature of the warpage, and a direction of the warpage.

24. The method according to claim 21, further comprising the step of:

storing information about an anomaly of the object and information about the deformation state in memory.

25. The method according to claim 21, further comprising the step of:

supplying the object with gas with a gas supplying unit from a backside of the object.

26. The method according to claim 25, further comprising the step of:

executing a simulation for supplying the gas.

27. The method according to claim 25, further comprising the step of:

mounting the object with an edge-grip-system, wherein:

the edge-grip-system comprises a plurality of bumps arranged on a plane facing the backside of the object, and the plurality of bumps are more tightly-packed towards a center of the object.

28. The method according to claim 27, wherein:

the edge-grip-system further comprises a rim for mounting a edge portion of the object, and the bumps are arranged at a position lower than a position of the rim.

29. The method according to claim 8, further comprising the step of:

exhausting the gas through an exhausting aperture, wherein the exhausting aperture is arranged between the rim and the bumps.

30. The method according to claim 25, further comprising the step of:

supplying the gas to change a warpage of the object to a target warpage.

31. The method according to claim 25, further comprising the step of:

changing a flow of the gas with a control unit.

32. The method according to claim 31, further comprising the steps of:

supplying the gas through a pipe;

providing a gated path with a first valve of the pipe; and controlling the first valve with a second valve.

33. The method according to claim 32, wherein the first valve is operated by compressed air and the second valve is an electromagnetic valve which controls supply of the compressed air.

34. The method according to claim 32, wherein the pipe is polished.

35. The method according to claim 31, wherein the flow control unit further comprises a filter arranged at flow path of the gas.

36. The method according to claim 31, further comprising the step of:

changing the flow of the gas according to a type of the gas.

37. The method according to claim 36, further comprising the step of:

changing the flow of gas by using a conversion-factor as a function of the type of the gas.

38. The method according to claim 31, further comprising the step of:

mounting the object with a chuck, wherein the flow control unit supplies the gas by providing a delay time until the chuck mounts the object.

39. The method according to claim 31, further comprising the step of:

rotating the object with a rotating unit, wherein the flow control unit stops supplying the gas providing a delay time until a number of rotations of the rotating unit decreases below a predetermined number of rotations.

40. The method according to claim 21, wherein the second light irradiating unit includes a broadband-light-source which outputs from visible-light to UV-light, or a white light source.

* * * * *